United States Patent
Grothe, Jr.

(10) Patent No.: US 8,686,349 B2
(45) Date of Patent: Apr. 1, 2014

(54) METHODS AND SYSTEMS FOR MATCHING PRODUCT IONS TO PRECURSOR IONS

(71) Applicant: Robert A. Grothe, Jr., Mountain View, CA (US)

(72) Inventor: Robert A. Grothe, Jr., Mountain View, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 13/792,826

(22) Filed: Mar. 11, 2013

(65) Prior Publication Data

US 2013/0187038 A1    Jul. 25, 2013

Related U.S. Application Data

(63) Continuation of application No. 13/319,395, filed as application No. PCT/US2010/032114 on Apr. 22, 2010, now Pat. No. 8,395,113.

(60) Provisional application No. 61/176,812, filed on May 8, 2009.

(51) Int. Cl.
  *H01J 49/26*   (2006.01)
  *B01D 59/44*   (2006.01)

(52) U.S. Cl.
  USPC ............ 250/282; 250/281; 250/283; 250/288

(58) Field of Classification Search
  USPC .................................. 250/282, 281, 283, 288
  See application file for complete search history.

(56) References Cited

U.S. PATENT DOCUMENTS

| | | | |
|---|---|---|---|
| 4,087,765 A | 5/1978 | Edelstein et al. | |
| 4,818,862 A | 4/1989 | Conzemius | |
| 5,538,897 A | 7/1996 | Yates, III et al. | |
| 6,924,478 B1 * | 8/2005 | Zubarev et al. | 250/282 |
| 8,237,106 B2 | 8/2012 | Castro-Perez et al. | |
| 8,395,113 B2 * | 3/2013 | Grothe, Jr. | 250/282 |
| 8,399,827 B1 * | 3/2013 | Grothe | 250/282 |
| 8,536,521 B2 * | 9/2013 | Grothe | 250/282 |
| 2006/0141528 A1 | 6/2006 | Aebersold et al. | |
| 2006/0192100 A1 | 8/2006 | Zubarev et al. | |
| 2006/0201881 A1 | 9/2006 | Marcus et al. | |
| 2006/0255259 A1 | 11/2006 | Zubarev et al. | |
| 2008/0001079 A1 | 1/2008 | Wang et al. | |

FOREIGN PATENT DOCUMENTS

| | | |
|---|---|---|
| EP | 1 047 108 A2 | 10/2000 |
| WO | WO 2008/003684 A1 | 1/2008 |

* cited by examiner

*Primary Examiner* — Nikita Wells
(74) *Attorney, Agent, or Firm* — Thomas F. Cooney

(57) ABSTRACT

Methods of tandem mass spectrometry are disclosed, characterized by: providing a mixture of precursor ions comprising a plurality of individually isolated ion types of respective selected m/z ratios; estimating an elemental composition for each precursor ion type based on its respective m/z ratio; generating a sample of fragment ions comprising a plurality of fragment ion types by fragmenting the plurality of precursor ion types of the mixture; generating a mass spectrum of the fragment ion types to determine a respective m/z ratio or m/z ratio range for each respective fragment ion type; estimating an elemental composition for each fragment ion type based on its respective m/z ratio or m/z ratio range; and calculating probabilities, for each precursor ion type, that a fragment ion type or a pair of fragment ion types was derived from said precursor ion type.

10 Claims, 9 Drawing Sheets

METHODS AND SYSTEMS FOR MATCHING PRODUCT IONS TO PRECURSOR IONS

CROSS REFERENCE TO RELATED APPLICATIONS

This application is a continuation of and claims, under 35 U.S.C. 120, the benefit of the filing date of U.S. patent application Ser. No. 13/319,395, now U.S. Pat. No. 8,395,113, which is the United States National Stage Application, under 35 U.S.C. 371, of International Application PCT/US2010/032114 having an international filing date of Apr. 22, 2010, which claims the benefit of the filing date, under 35 U.S.C. 119(e), of U.S. Provisional Application 61/176,812, filed on May 8, 2009, all of said related applications hereby incorporated by reference herein in their entirety.

TECHNICAL FIELD

This invention relates to methods of and systems for obtaining and analyzing tandem mass spectrometry data.

BACKGROUND ART

Structural elucidation of ionized molecules of complex structure, such as proteins is often carried out using a tandem mass spectrometer, where a particular precursor ion is selected at the first stage of analysis or in the first mass analyzer (MS-1), the precursor ions are subjected to fragmentation (e.g., in a collision cell), and the resulting fragment (product) ions are transported for analysis in the second stage or second mass analyzer (MS-2). The method can be extended to provide fragmentation of a selected fragment, and so on, with analysis of the resulting fragments for each generation. This is typically referred to an $MS^n$ spectrometry, with n indicating the number of steps of mass analysis and the number of generations of ions. Accordingly, $MS^2$ corresponds to two stages of mass analysis with two generations of ions analyzed (precursor and products). A resulting product spectrum exhibits a set of fragmentation peaks (a fragment set) which, in many instances, may be used as a fingerprint to derive structural information relating to the parent peptide or protein.

Unfortunately, the above-described procedure of sequentially isolating and fragmenting each precursor ion, in turn, may not provide great enough throughput for analyses of complex mixtures of biomolecules. For emerging high-throughput applications such as proteomics, it is important to provide as-yet unattainable speeds of analysis, on the order of hundreds of MS/MS spectra per second. The throughput may be increased by obtaining spectra containing a mixture of fragment sets (a "multiplexed" spectrum), the mixture produced by fragmenting multiple parent ions simultaneously, instead of sequentially. The final multiplexed spectrum contains products from a mixture of precursors, in contrast to an MS/MS spectrum in which the products come from a single isolated precursor.

Procedures for obtaining and analyzing multiplexed spectra can potentially reduce hardware complexity, since an upstream mass analyzer may be eliminated. Analysis of product ions produced by multiple precursor ions can also better utilize the spectral bandwidth of high-resolution mass analyzers, such as Fourier Transform Ion Cyclotron Resonance and Orbitrap mass spectrometers. However, interpretation of the potentially large number of fragment peaks in the resulting multiplexed spectrum can be challenging.

Multiplexing is a general strategy for increasing throughput when the capacity of a communication channel far exceeds what is required to send an individual message at a specified fidelity. Under certain conditions, it may be possible to send multiple messages through the channel simultaneously without appreciable information loss. In communication systems, the individual signals are encoded before being combined at the transceiver to allow the detected signal to be "demultiplexed" or separated into the original component signals at the receiver. The two most common examples of multiplexing are time and frequency multiplexing. In either case, the channel is partitioned into discrete sub-channels.

In the field of mass analysis, the simultaneous measurement of multiple ions by a Fourier transform mass spectrometer (e.g., LTQ-FT or LTQ-Orbitrap) is an example of frequency multiplexing. The signal from each ion populates a narrow band (of fixed width) in the frequency spectrum of the Fourier-transformed transient signal. Typically, these bands are distinct, i.e., non-overlapping, and can be trivially separated. In theory, the channel capacity of a Fourier-transform mass spectrum is the ratio of the spectrum bandwidth divided by the bandwidth of an individual ion signal.

A Fourier transform mass spectrum has sufficient channel capacity to allow the simultaneous measurement of thousands of distinct ion masses, corresponding to neutral molecules present in a sample. However, the "code", i.e., representing molecules by their masses, is degenerate, since multiple distinct molecules (e.g., isomers) can have identical elemental compositions and therefore identical masses. Furthermore, molecules with masses that are distinct, but differ by less than the nominal mass accuracy, can be misidentified.

To overcome this limitation, additional information about the molecule's identity can be obtained, by breaking the molecule into fragments and measuring the masses of these product ions. The covalent structure of a molecule, which distinguishes it from its isomers, can be inferred from a sufficiently informative MS/MS spectrum and perhaps additional a priori information. Commercially available software products such as MASCOT and SEQUEST have been used to identify peptides by matching a list of masses extracted from such spectra to predicted product ion masses generated from protein sequences stored in proteomic databases. These programs often provide correct identifications even when the product ions are measured with only unit mass accuracy and resolution. Unfortunately, in conventional practice, an entire spectrum is used to measure the product ions from one precursor. This represents a dramatic bottleneck in throughput.

The present invention takes advantage of the concept that the additional information provided by high-mass-accuracy (e.g. 1 part-per-million (ppm) rather than unit mass accuracy) and high-resolving-power measurements of product ions can support mass-spectral de-multiplexing. Such de-multiplexing permits greater sample throughput. In other words, the availability of high-resolution and high-accuracy spectrometers makes it possible, in certain instances, to identify multiple precursor molecules from a single high quality spectrum that contains a mixture of product ions derived by fragmentation of these multiple precursors. The additional mass accuracy of the fragments can enable development of algorithms to discover the correct assignment of product ions to precursors while also compensating for uncertainties, errors, and losses associated with the assignment process.

Such analysis of multiplex MS/MS spectra may make use of existing algorithms, such as MASCOT and SEQUEST to subsequently identify each of the precursors. A preprocessing step would partition product ions from a multiplex spectrum into multiple virtual MS/MS spectra, each of which would contain product ions from only a single precursor. Formation of virtual MS/MS spectra according to the invention thus represents "synthetic isolation" of precursors.

A previously described MS/MS demultiplexing method (PCT International Patent Application Publication WO 2008/003684 A1; inventor, Scigocki) has described the use of "correlation laws" to map pairs, triplets, or arbitrarily large subsets of product ions to a precursor ion. A correlation law essentially states that the masses of the product ions (formed by multiplying each mass-to-charge ratio by an integer representing the unknown charge of the ion) sum to the mass of the precursor ion (also formed by multiplying the mass-to-charge ratio by some integer). However, the observed mass-to-charge ratios contain measurement errors so that a "proximity criterion" is necessary to allow for small deviations from the ideal correlation law. In general, because the charges for the precursors and products are unknown, there could be a large number of correlation laws (planes passing through the space formed by combinations of product mass-to-charge ratios). It is plausible that some of the correlation laws may pass within the tolerance of the observed mass-to-charge ratios of some product ions simply by random chance leading to false assignments of product ions to precursors.

From the foregoing discussion, there is a need in the art for improved methods and apparatus for obtaining and resolving multiplexed tandem mass spectra. The present invention addresses such a need.

DISCLOSURE OF INVENTION

According to first aspect of the invention, there is provided a first method for obtaining and interpreting multiplex product ion spectra. The first method assumes high mass accuracy spectra of 1) intact precursor ions and 2) the product ions that result from simultaneously fragmenting the precursors. It is also assumed that the masses of both precursors and products are measured to sufficient accuracy that their elemental compositions can be determined (or at least reduced to a small number of possibilities).

The method computes the probability a given product arose from a given precursor for all product-precursor pairs on the basis of a probabilistic model that assumes no knowledge of the covalent structure of the precursor. In this model, products are generated by uniformly random selection of atoms from the precursor. The resulting distribution of product elemental compositions is multinomial over the various types of elements occurring in the precursor.

These probabilities are used to assign product ions to precursors, thus generating synthetic MS/MS spectra that can be interpreted separately in parallel by existing algorithms. The candidate identifications produced by these algorithms can be combined to form synthetic multiplex product ion spectra that can be directly matched against the observed multiplex spectrum to determine the most likely set of precursor identifications.

According to a second aspect of the invention, a second method is provided in which robust detection of pairwise complementary product ions uses at least partially-known elemental composition (EC) analysis. In spectra with high mass accuracy and resolving power, the ECs of the product and precursor ions can be inferred. When the sum of two product ion ECs is an exact match to a given precursor ion EC, it is possible to confidently identify these product ions as complementary and assign them to the corresponding precursor. High mass accuracy and resolving power enables charge-state and elemental composition determination. Elemental composition, in theory, provides an exact match between pairs of product ions and precursor ions.

Some embodiments in accordance with the invention comprise methods of tandem mass spectrometry (MS/MS) for use in a mass spectrometer, the methods characterized by the steps of: (a) providing a sample of precursor ions comprising a plurality of ion types, each ion type comprising a respective range of masses; (b) generating a mass spectrum of the precursor ions using the mass spectrometer so as to determine a respective mass value or mass value range for each of the precursor ion types; (c) estimating an elemental composition for each of the precursor ion types based on the mass value or mass value range determined for each respective ion type; (d) generating a sample of fragment ions comprising plurality of fragment ion types by fragmenting the plurality of precursor ion types within the mass spectrometer; (d) generating a mass spectrum of the fragment ion types so as to determine a respective mass value or mass value range for each respective fragment ion type; (e) estimating an elemental composition for each of the fragment ion types based on the mass value or mass value range determined for each respective fragment ion type; and (f) calculating a set of probability values for each precursor ion type, each probability value representing a probability that a respective fragment ion type or a respective pair of fragment ion types was derived from the precursor ion type. Some embodiments may include a step (g) of generating a synthetic MS/MS spectrum for each respective precursor ion type based on the calculated probability values. Some embodiments may further include an additional step (h) of providing at least one of the synthetic MS/MS spectra as input to a peptide identification software product, such as MASCOT or SEQUEST, so as to identify a peptide in a sample from which the sample of precursor ions is derived.

In some embodiments in accordance with the invention, the step (d) of generating a sample of fragment ions comprising plurality of fragment ion types may comprise the steps of: (d1) selecting a subset of the precursor ion types, the subset comprising a group of precursor ion types of interest; (d2) isolating a precursor ion type of interest in a mass analyzer of the mass spectrometer; (d3) transferring the isolated precursor ion type of interest to a collision cell or a reaction cell of the mass spectrometer; (d4) repeating steps (d2) and (d3) for each remaining precursor ion type of interest so as to provide a mixture of precursor ion types of interest; and (d5) generating the sample of fragment ions by simultaneously fragmenting the precursor ions of interest in the collision cell or reaction cell. Alternatively, the fragment ions may be generated by fragmenting the plurality of precursor ions simultaneously, possibly in a collision cell or reaction cell.

In some embodiments in accordance with the invention, the step (f) of calculating a set of probability values for each precursor may comprise the steps of: (f1) estimating a variance of the mass of each precursor ion type and each fragment ion type; (f2) estimating a variance of a mass difference for each possible triplet of ion types, the triplet consisting of one precursor ion type and two fragment ion types; and (f3) retaining, for consideration, only those triplets of ion types for which the mass difference is equal to zero within a certain multiple of the respective variance of the mass difference. The following set of steps may also be included: (f4) estimating respective elemental compositions for the precursor ion type and each fragment ion type of each retained triplet; (f5) estimating a probability of the correctness of each respective estimated elemental composition estimated in step (f4); and (f6) calculating a probability that the two fragment ion types were formed by fragmentation of the precursor ion type of each retained triplet, based on the estimated probabilities of the correctness estimated elemental compositions.

The mass spectrometer may comprise an ion cyclotron resonance mass spectrometers or an Orbitrap mass spectrometer and may provide a mass accuracy of 1 ppm or better. It may comprise a single mass analyzer or, alternatively, a first mass analyzer and a second mass analyzer comprising higher accuracy than the second mass analyzer. In the latter case, an ion storage device may be provided between the first and second mass analyzers.

BRIEF DESCRIPTION OF DRAWINGS

The above noted and various other aspects of the present invention will become apparent from the following description which is given by way of example only and with reference to the accompanying drawings, not drawn to scale, in which.

MODES FOR CARRYING OUT THE INVENTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-4 taken in conjunction with the following description.

Figure 1A:
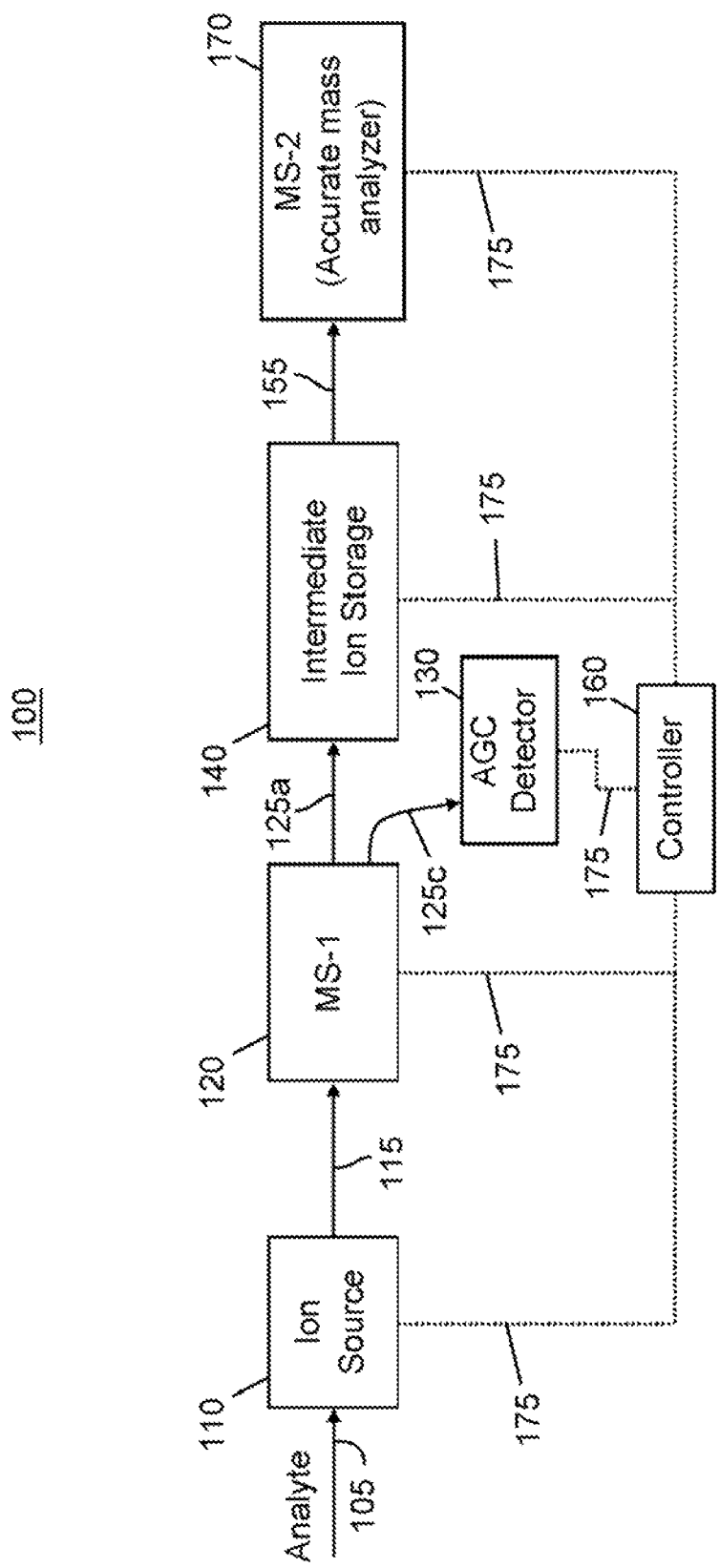
FIG. 1A is a schematic illustration of a first example of a generalized tandem mass spectrometer system on which the invention according to some of its aspects may be practiced.

A first example of a generalized tandem mass spectrometer system 100 on which the invention according to some of its aspects may be practiced is shown in FIG. 1A. Analyte material 105 is provided to a pulsed or continuous ion source 110 so as to generate ions 115. The ions are admitted to a first mass analyzer (MS-1) 120 that has mass analysis and mass selection functionality and in which, optionally, fragmentation may be performed. For instance, the first mass analyzer MS-1 may comprise an ion trap. Alternatively, a separate reaction cell (not shown in FIG. 1A) may be used to perform fragmentation. Ion source 110 could be a MALDI source, an electrospray source or any other type of ion source. In addition, multiple ion sources may be used. Also, the mass analyzer MS-1 120 may be preceded by any number of other stages of mass analysis, and/or ion manipulation.

It is to be noted that, in the system of FIG. 1A as well as in systems illustrated in subsequent drawings, ions are transferred from one component to the next via ion optics (e.g., RF multipoles) which, in most cases, are not specifically illustrated. Moreover, the drawings do not show the electrodes of the various parts-that are used to guide and/or trap ions within those parts.

All embodiments of the invention may be operated with an automatic gain control (AGC) detector 130 (see FIG. 1A, for instance) to trap an appropriate number of ions. Any of the known AGC methods may be used to determine the optimum ionization time for fills of the downstream intermediate ion storage 140 or the accurate mass analyzer MS-2 170. Accordingly, a proportion of ions exiting MS-1 may be diverted along path 125c to AGC detector 130. Otherwise, ions are transferred from MS-1 along path 125a to the intermediate ion storage 155.

In this application, AGC is interpreted in a most general way as a method of determining an optimum fill time based on sampling a set of ions. Therefore, it includes not only methods based on information from a pre-scan or previous scan, but includes other methods of measuring numbers of ions such as a current sensing grid that intercepts (preferably uniformly) an ion beam; sensing induced currents; sensing scattered ions, for example on apertures; sensing secondary electrons; and using a previous analytical scan taken by the first mass analyzer 120. Ions produced using the optimum ionization time may be fragmented in either the first mass analyzer 120 or a separate reaction cell, for example, by collision-induced dissociation.

Selected ions are transferred from the first mass analyzer 120 along path 125a into the intermediate ion storage device 140 where they are captured and trapped. The intermediate ion storage device 140 may comprise, for instance, an ion trap device. Ions released from the intermediate ion storage device 140 are transferred along path 155 to an accurate mass analyzer (MS-2) 170. The accurate mass analyzer may receive, for analysis, either unfragmented precursor ions, a set of ions formed by fragmentation of a single selected precursor ion, or a mixture of a plurality of sets of ions, each such set formed by fragmentation of a respective precursor ion. The accurate mass analyzer has sufficiently high m/z resolution to resolve all species in such mixed ion populations. Examples of suitable accurate mass analyzers are ion cyclotron resonance mass spectrometers and Orbitrap (a type of electrostatic trap) mass spectrometers.

Continuing with the discussion of FIG. 1A, a controller 160, which may comprise a general purpose computer or, perhaps, a specialized electronic logic device, is electronically coupled to all other components along electronic control lines 175. The electronic control lines 175 may send control signals from the controller 160 to the mass spectrometers, intermediate ion storage device, ion source, the various ion optics, etc. in order to control the coordinated operation of these components. For instance, the controller may send signals to set potentials on the electrodes of the various parts at the various appropriate times. The electronic control lines 175 may also transmit signals from one or more of the components of the system 100 back to the controller 160. For instance, the controller 160 may receive signals from the AGC detector 130 and from the accurate mass analyzer 170, such signals relating to number of ions detected.

Figure 1B:
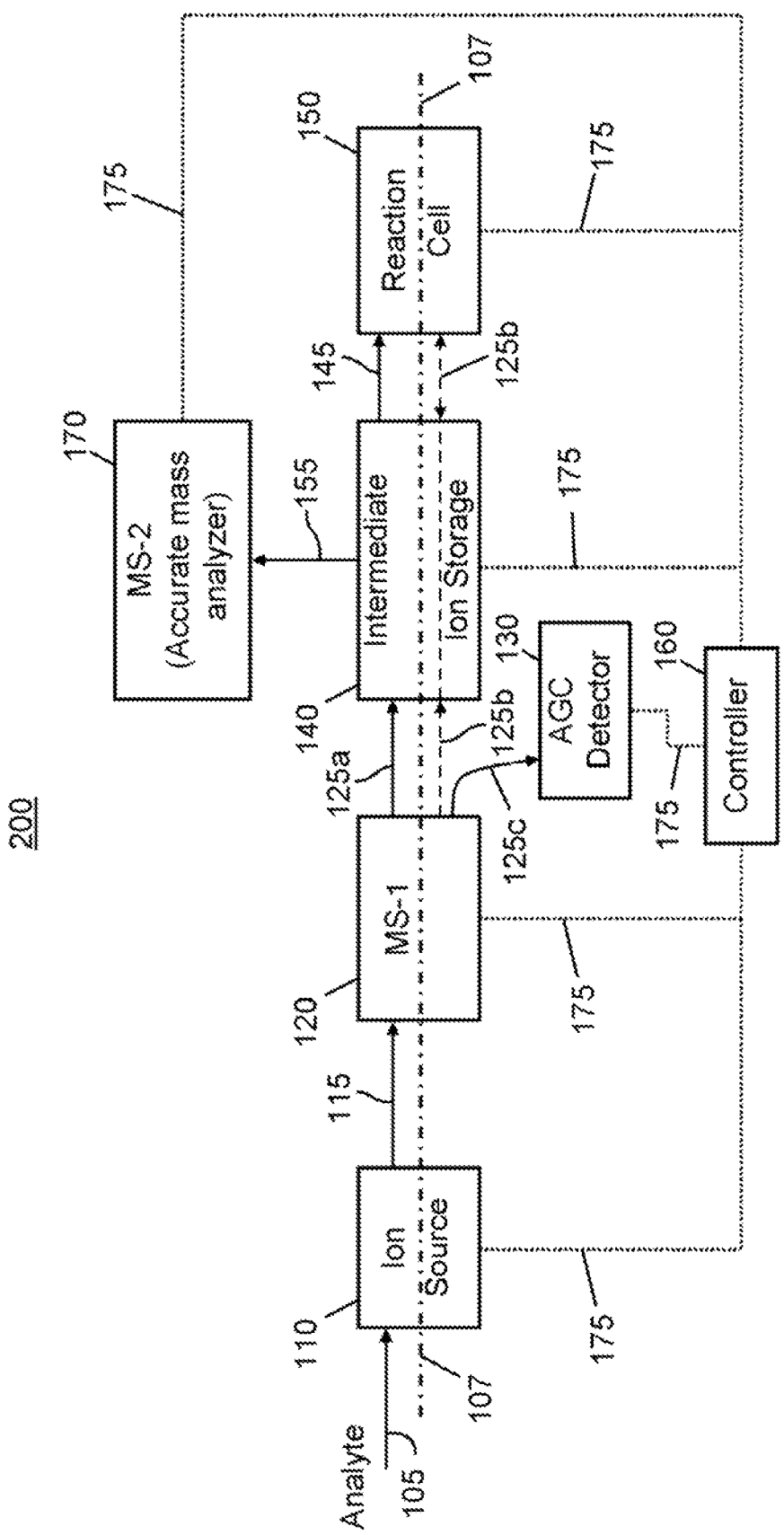
FIG. 1B is a schematic illustration of a second example of a generalized mass spectrometer system on which the invention according to some of its aspects may be practiced.

A second example of a generalized mass spectrometer system 200 on which the invention according to some of its aspects may be practiced is shown in FIG. 1B. The system 200 shown in FIG. 1b comprises all of the components as described with reference to the mass spectrometer system 100 (FIG. 1A), with similar reference numbers thus being used in the two drawings. With reference to FIG. 1B, however, it is to be noted that, although most components of the mass spectrometer system 200 are positioned on the longitudinal "axis" 107 (shown as a dot-dash line), the accurate mass analyzer MS-2 is positioned off of this axis. Further, a reaction cell for fragmentation of ions is disposed along axis 107 at the side of the intermediate ion storage device opposite to MS-1. Although the curve 107 is shown as a straight line and referred to as an "axis", it should be noted that, in practice, at least a portion of this curve may not, in fact, be linear.

The system 200 shown in FIG. 1B (and also the system 300 shown in FIG. 1C) provides for two types of ion pathways between the first mass analyzer MS-1 and the accurate mass analyzer MS-2, corresponding to two respective modes of operation. In a first mode of operation, selected ions are delivered along pathway 125a from MS-1 to the intermediate ion storage device 140 where they are trapped. Once a suitable time delay has passed, the controller 160 transports the ions to the reaction cell 150. In a second, alternative, mode of operation, the intermediate ion storage device 140 is used merely as an ion guide ("transmission mode") such that ions are transferred along pathway 125b (which may, in fact be coincident with path 125a but which is shown offset from that pathway, for clarity) from MS-1 to the reaction cell 150. The intermediate ion storage device 140 may be filled with gas, thereby reducing the energy of the ions through collisional cooling as they pass through the intermediate ion storage device and enter the reaction cell 150.

Precursor ions may be fragmented in the reaction cell. Ion fragmentation may be effected by any suitable fragmentation technique, such as collision-induced dissociation (CID), electron transfer dissociation (ETD), electron capture dissociation (ECD) or infrared multiphoton dissociation (IRMPD). The resulting fragment ions (if any) or precursor ions (if any) are then transferred, in the opposite direction, back along path 125b from the reaction cell to the intermediate ion storage device 140. After storage in the intermediate ion storage device 140 for an appropriate time, these fragment ions are transferred to the accurate mass analyzer 170 for analysis along pathway 155. Multiple fills of the accurate mass analyzer 170 may be formed using different respective processing techniques (for instance, high energy versus low energy fragmentation) in the reaction cell 150. This flexibility provides the capability of performing both precursor ion as well as fragment ion analyses using the accurate mass analyzer.

Automatic gain control, as facilitated by the AGC detector 130, may be used to control the ion abundance in the intermediate ion storage device 140, the reaction cell 150 or the accurate mass analyzer 170. Automatic gain control is described in U.S. Pat. No. 5,107,109 and U.S. Pat. No. 6,987,261, both of which are incorporated by reference herein in their entirety.

Figure 1C:
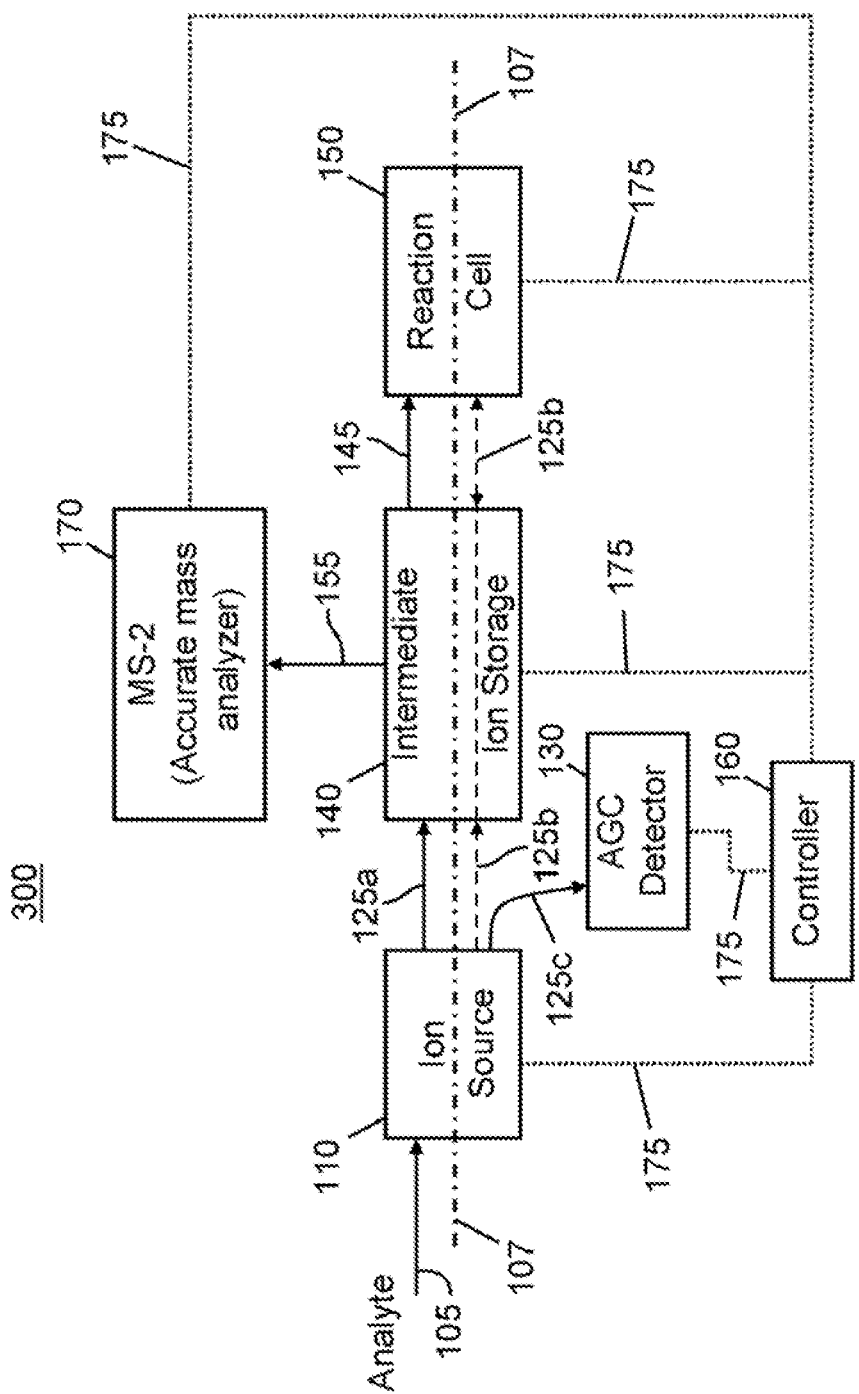
FIG. 1C is a schematic illustration of a third example of a generalized mass spectrometer system on which the invention according to some of its aspects may be practiced.

FIG. 1C illustrates a third example of a generalized mass spectrometer system 300 on which the invention according to some of its aspects may be practiced. The mass spectrometer system 300 is similar to the system 200 illustrated in FIG. 1B, except that the system 300 does not comprise a first mass spectrometer MS-1. Thus, in the system 300, the ion source 110 delivers, to either or both of the intermediate ion storage device 140 and the reaction cell 150, streams or pulses of ions which are not pre-selected or pre-isolated according to their m/z.

Figure 2A:
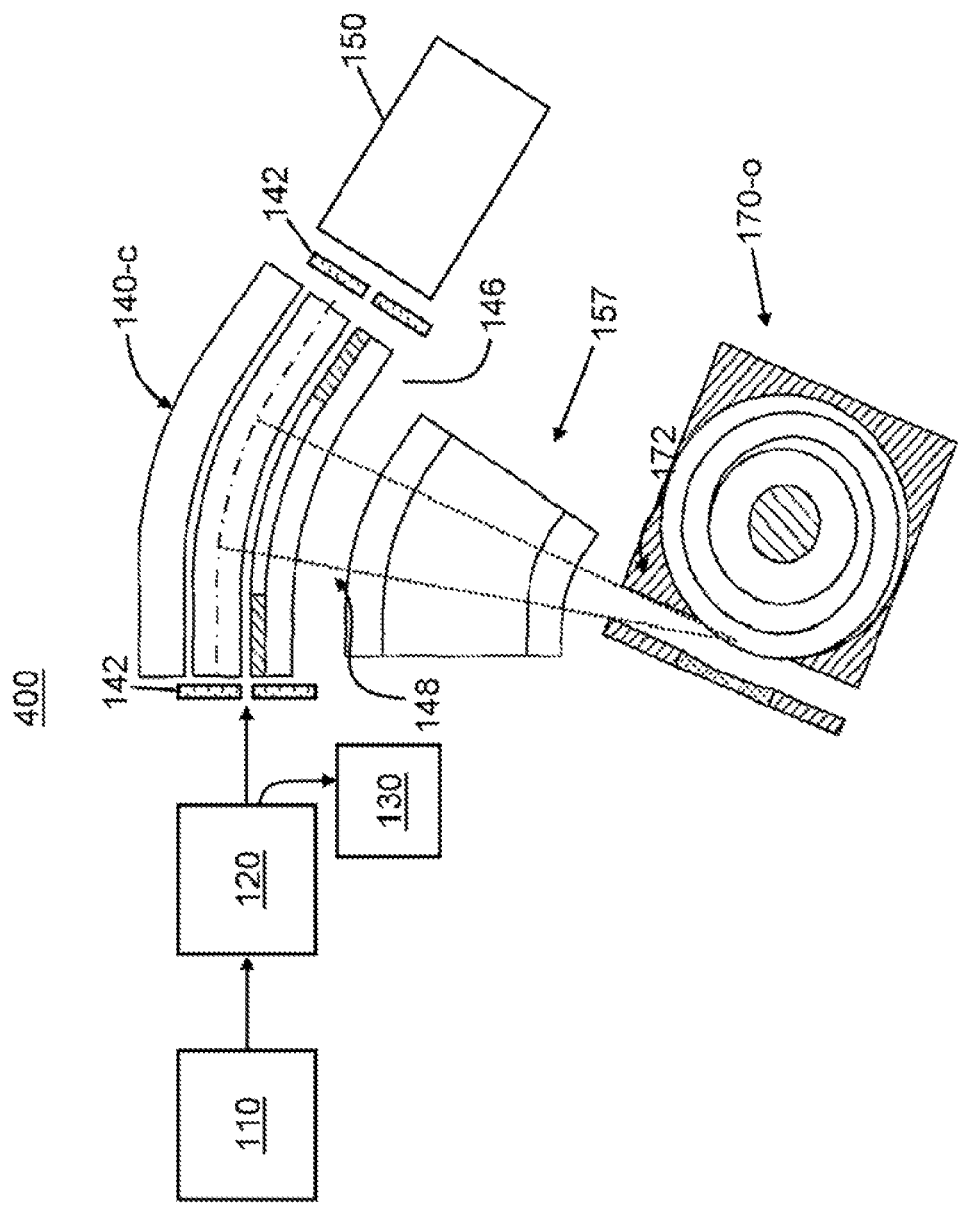
FIG. 2A is a schematic illustration of a particular mass spectrometer system on which the invention according to some of its aspects may be practiced, the system including an Orbitrap mass analyzer.

FIG. 2A is a diagram of a particular example of a mass spectrometer system of the type earlier shown in FIG. 1B. In the mass spectrometer 400 shown in FIG. 2A, the intermediate ion storage device comprises a curved quadrupolar linear ion trap (shown as reference number 140-c) bounded by gates 142 at respective ends. The curvature of the intermediate ion storage device 140-c is used such that, when the ions are ejected off axis, the ions are radially convergent. The ions are ejected off-axis in the direction of the entrance 172 to an Orbitrap mass analyzer 170-o, which serves as the accurate mass analyzer in this example. The ions are ejected from the curved trap 140-c through an aperture 148 provided in an electrode 146 of the curved trap 140-c and through further ion optics 157 that assist in focusing the emergent ion beam. It will be noted that the curved configuration of the intermediate ion storage device (i.e., the curved quadrupolar linear ion trap 140-c in this particular instance) also assists in focusing the ions. The curved linear ion trap 140-c is inherently useful as it allows rapid ejection of pulses of ions to the mass analyzer 170-o with little, if any, further shaping required.

In operation, ions are generated in the ion source 110 and transported through ion optics so as to be accumulated temporarily in MS-1 120 according to e.g. US20030183759 or U.S. Pat. No. 6,177,668. MS-1 120 may contain an inert gas (i.e., 1 mTorr of helium) such that the ions lose some of their kinetic energy in collisions with the gas molecules.

Either after a fixed time delay (chosen to allow sufficient ions to accumulate in MS-1 120) or after sufficient ions have been detected in MS-1 120 (possibly through detection with AGC detector 130), ions are ejected from MS-1 120 so as to travel into the intermediate ion storage device 140-c. As discussed previously, ions may pass through the intermediate ion storage device 140-c into the reaction cell 150 where they are processed before being returned back to the intermediate ion storage device 140-c.

Figure 2B:
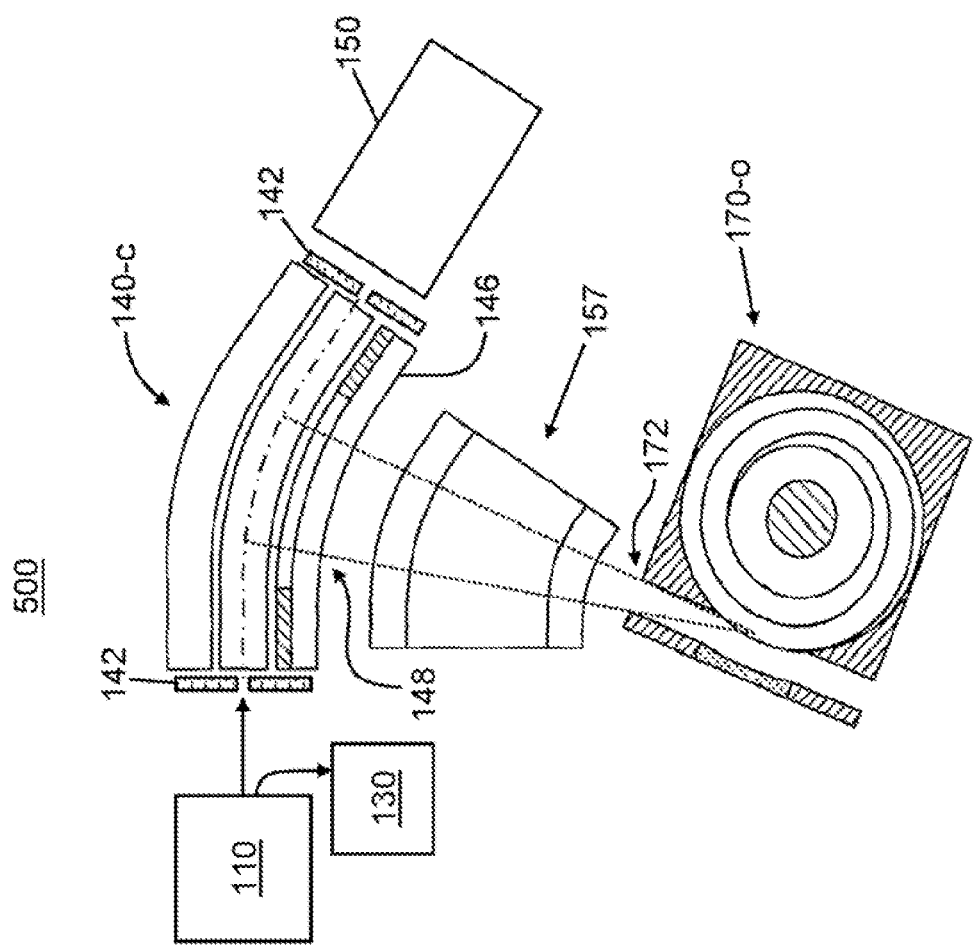
FIG. 2B is a schematic illustration of another particular mass spectrometer system on which the invention according to some of its aspects may be practiced, the system including an Orbitrap mass analyzer.

FIG. 2B is a diagram of a particular example of a mass spectrometer system of the type earlier shown in FIG. 1C. The system 500 shown in FIG. 2B comprises the components shown in FIG. 2A except for the first mass analyzer MS-1. Thus, ions of a range of m/z may be passed through to the intermediate ion storage device 140-c, to the reaction cell 150 and to the accurate mass analyzer 170-o.

In the following discussion, inventive algorithms are described which provide the enabling technology for MS/MS multiplexing: matching product ions observed in a multiplex MS/MS spectrum to precursor ions observed in an MS spectrum. As used in this specification, an "ion type" includes all ions having the same charge state and identical numbers of atoms of each element—for instance, the same number of carbon atoms, the same number of nitrogen atoms, etc. Frequently, each ion type may comprise a respective range of masses because of the distribution of different isotopes of the various atoms within the atom. Occasionally, however, an ion type may consist of a single, discrete mass. For instance, mass spectra may not exhibit isotope peaks if a single mass-to-charge ratio was previously selected and isolated. A monoisotopic peak represents only the principal isotopes of the atoms of which the ion is composed.

The fundamental challenge of the "all ions" workflow is the interpretation of the multiplex fragmentation spectrum. The problem is analogous to spilling the pieces from a stack of puzzle boxes into a pile and trying to assemble all the puzzles at the same time. One approach to the problem is use clues about the puzzle pieces to place each piece back into its box. If this could be accomplished, then the problem can be solved by repeatedly assembling a single puzzle from its pieces. Likewise, if there were a mechanism for mapping each product ion to its precursor ion then existing methods for MS/MS analysis of product ions from isolated precursors could be used repeatedly to identify each precursor.

EXAMPLE 1

Elemental Compositions Known

Continuing the puzzle analogy, the puzzle pieces may contain clues that allow them to be grouped correctly into families, including the texture or color on the backs of the pieces, the material, or the distribution of colors or sizes. At first glance, ions would not seem to provide such clues. However, the elemental compositions of ions would contain information about their precursor ion of origin. For example, a product ion containing a sulfur atom cannot arise from a precursor without sulfur. Similarly, a product ion containing six nitrogen atoms cannot arise from a precursor atom containing five or fewer nitrogen atoms. These are examples that place absolute constraints in the mapping of certain products to precursors. In general, the precursor must contain at least as many atoms of each elemental type as appears in its putative products. In cases where this criterion is not satisfied, the probability that the product originated from that precursor is exactly zero.

The analysis can be further generalized to include statements or relative, rather than absolute, probability. For example, a product that is almost identical to its precursor (e.g., differs by a single methyl group or a single amino acid residue) is highly likely to have originated from the precursor even though it is possible that it may have originated from a much larger molecule.

Consider two precursor molecules A: $C_{10}H_{14}O_6$ and B: $C_{30}H_{60}N_6O_4$ and a product X: $C_8H_{10}O_4$. Although it is possible that product X came from precursor B, it is considerably more likely to have come from precursor A, based upon their elemental compositions and the laws of probability. If no structural information is available about A and B, the distribution of product elemental compositions could be modeled by selecting atoms from the precursors at random. In that case, elements in the product would tend to occur in similar proportions as in the precursor. In the present situation, production of product X by randomly selecting 22 of the 100 atoms from B would be unlikely to result in a collection that contains none of its six nitrogens and all of its four oxygens. In contrast, the selection of 8 of 10 carbons, 10 of 14 nitrogens, and 4 of 6 carbons (as would be required if X was a product of A) is a much more likely outcome.

The inventive method formalizes the reasoning described above to evaluate the probability that a given product would have arisen from each of N possible precursors given only the elemental composition of the product and the precursors. First, consider the distribution of products that would arise from a given precursor. Assume that the product and precursor are identified only by their elemental compositions. That is, no structural information is available about either the precursor or the product. In other words, all structures are equally likely.

In this case, the distribution of products is mathematically equivalent to the outcomes of drawing colored balls from an urn without replacement. The balls placed in the urn (before drawing any out) represent atoms in the precursor. The colors of the balls placed in the urn are chosen to represent the different elemental types of atoms that occur in the precursor; the number of balls of a given color is chosen to match the number of atoms of the corresponding type occurring in the precursor. Balls drawn at random out of the urn without replacement represent the atoms that would occur in a randomly generated product. For example, the distribution of products containing exactly N atoms could be generated by drawing N balls from the urn without replacement and repeated such a trial of N selections a large number of times. Fortunately, it is possible, and straightforward, to calculate the distribution of outcomes in the limit of an infinite number of trials for an arbitrary value of N (the number of atoms in the product) and an arbitrary precursor elemental composition.

For example, consider a precursor "a" made up of atoms of K different types: $a_1$ atoms of type 1, $a_2$ atoms of type 2, and in general, $a_k$ atoms of type k, where k is an integer between 1 and K. Assuming that it is possible to specify the types of atoms 1 to K, then the elemental composition of a can be represented by the K-component vector $a=(a_1, a_2, \ldots, a_K)$. Each $a_k$ must be a positive integer.

Likewise, consider a potential product "X" made up of the same K types of atoms as the precursor. The elemental composition of X may be represented by the vector $x=(x_1, x_2, \ldots, x_K)$. For X to be a candidate product of a, each $x_k$ must be a non-negative integer with the constraint that $x_k \leq a_k$. For notational shorthand, let A be the sum of the $a_k$'s (Equation 1) and let X be the sum of the $x_k$'s (Equation 2). Then, A and X denote the number of atoms in X and a respectively.

$$A = \sum_{k=1}^{K} a_k \quad (1)$$

$$X = \sum_{k=1}^{K} x_k \quad (2)$$

The probability of generating product X with elemental composition x from precursor a is given by Equation 3: An additional constraint is that the product has X atoms.

$$P(x \mid a, X) = \frac{\prod_{k=1}^{K} \binom{a_k}{x_k}}{\binom{A}{X}} \quad (3)$$

The denominator of the above equation denotes the number of ways to draw X atoms from A atoms. Each factor in the numerator gives the number of ways to draw $X_k$ atoms of type k from $a_k$ atoms of type k. When A is divisible by X, it can be shown that the most likely product is (X/A)a. That is, the most likely product is one that has atoms occurring in the same proportion as the precursor. In general, when A is not divisible by X, the most likely product(s) are vectors with integer components that are "closest" to the vector (X/A)a. The equation above can be thought of as a mathematical statement of the intuitive notion that products have compositions that are similar to their precursor.

Equation 3 above states the distribution of products containing exactly X atoms. Equation 4 below gives the distribution of products of arbitrary size. The product on the right-hand side reflects that generating a product can be modeled abstractly as two sequential independent processes: selecting a product size X and then selecting a product elemental composition x, composed of X atoms. The first-term p(X/A) is the probability that a precursor of A atoms would produce a product of X atoms. The product size is assumed to depend only on the size of the precursor, and not its elemental composition.

$$P(x|a) = P(X|A)P(x|a,X) \quad (4)$$

Without knowledge of the precursor structure, the most reasonable assumption about the product size distribution is uniformity. That is, the probability of X is 1/A for all X between 1 and A, and zero otherwise (Equation 5).

$$P(X|A) = \begin{cases} 1/A & x \in \{1, \ldots, A\} \\ 0 & \text{otherwise} \end{cases} \quad (5)$$

For example, a uniform distribution of product sizes would be generated by selecting a bond uniformly at random from the linear precursor structure at random and breaking it. Likewise, a uniform distribution of product sizes would result from first selecting a randomly generated precursor structure of a given elemental composition and then breaking a randomly selected bond. Equation 6 results from inserting into Equation 4 the uniform factor given in Equation 5.

$$P(x|a) = \frac{1}{A} P(x|a, X) \quad (6)$$

More-realistic distributions of product sizes could be used instead of the uniform distribution to take into account various effects, either observed or theoretical, that impose a bias upon observed product sizes. For example, a smaller molecule would be less likely to contain a charge-carrying site than a larger molecule. However, a larger ion would be more likely to contain an unstable bond that would eliminate the intact species before it could be observed. Without a more detailed analysis, it is not clear which of these effects would be more significant.

Another refinement of the model is a consideration of charge mobility. In the case of an immobile charge, the ion's charge state would be considered as component k+1 of the vector. Thus, the charge on the ion would tend to partition in the same way as the atoms, so that a product that is half the size of the precursor would be most likely to have half its charge. However, if the charge is absolutely mobile, spending an equal amount of time associated with any atom, then all products could be observed. Smaller products would be seen at proportionately lower abundance than larger products since the probability that the charge was residing in a given region of the molecule at the instant of fragmentation would vary in proportion to the product size.

Equation 6 above provides the distribution of products that a given precursor would produce. It is an intermediate step in, computing the probability that an observed product originated from a particular precursor (i.e., the desired quantity). The latter quantity may be derived in terms the former expression (derived above) by using Bayes' Theorem. The result is shown in Equation 7.

$$P(a|x) = \frac{P(a)P(x|a)}{\sum_{a'} P(a')P(x|a')} \quad (7)$$

In the above equation, vectors a and x denote the elemental composition of one of the observed precursors and observed products respectively. The denominator is a normalizing factor that is the sum over all observed precursor elemental compositions. These precursors are indexed by the variable a'. The expression P(a|x) is evaluated using the equation derived above for each pair (x, a) formed by selecting one of the observed products and one of the observed precursors.

An important special case is that all precursors are equally likely. In this case, the value of P(a) is equal for all candidates and the expression for the probability is given by Equation 8.

$$P(a|x) = \frac{P(x|a)}{\sum_{a'} P(x|a')} \quad (8)$$

The above equation assigns probabilities to the candidate precursors that sum to one. However, the equation does not take into account the possibility that the product comes from none of candidates or from more than one of them. These considerations are relatively minor effects that do not significantly diminish the utility of the calculated probability estimates in most cases.

Note that uncertainties in determining the elemental composition of either the precursors or the product ions can also be accommodated by computing the probability-weighted sum of either Equation 7 or 8, where the sum is taken over the candidate elemental compositions and each weight is the probability associated with a particular candidate.

Figure 3:
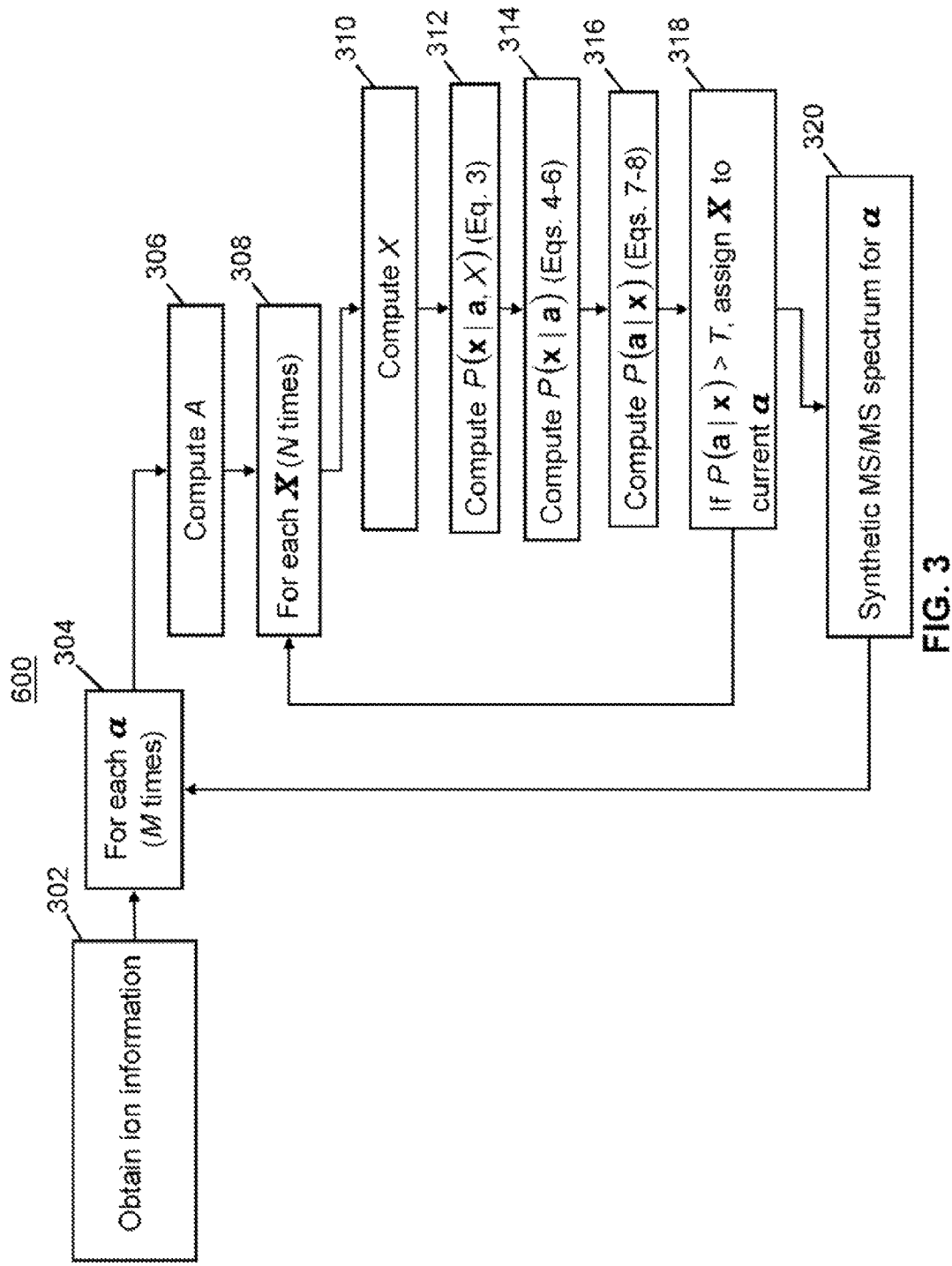
FIG. 3 is a flow chart of a first method for matching mass spectrometry precursor and product ions in accordance with the present invention.

FIG. 3 is a flow chart of a first method, method 600, in accordance with the present invention and the above discussion. The method 600 provides an implementation of the calculations discussed above for matching mass spectrometry precursor and product ions. In the initial step, step 302, a sample of interest is ionized and these ions and fragments thereof are analyzed by tandem mass spectrometry. This analysis yields the masses of a set of M sample-derived ions (precursor ions) and a set of N product (fragment) ions produced by decomposition of the precursor ions. From these experimentally obtained masses, the elemental compositions of each precursor ion and each product ion may, in some instances, be assigned. This yields a set of M precursor elemental compositions and N product elemental compositions in addition to the M precursor masses and N product masses determined by the mass analysis.

The lists of precursor and product ionic masses and elemental compositions obtained in step 302 of the method 600 (FIG. 3) are utilized in calculation steps 304-318. The step 304 is an initiation step for a first loop. In step 304, each precursor ion, $a_i$, is presented for consideration in sequence, such that each iteration of the subsequent steps in the loop, steps 306-320 produces a set of assignments of the product ions most likely to have been produced by fragmentation of $a_i$.

In step 306, the value of $A_i$ (the appropriate value of A for the precursor ion $a_i$) is calculated from Eq. 1. Subsequently, step 308 is an initiation step for a second loop (an inner loop)

that is nested within the first loop. In step 310, each product ion, $X_j$, is presented for consideration in sequence, such that each iteration of the subsequent steps 312-316 yields a numerical probability that the product ion under consideration, $X_j$, was produced by fragmentation of $a_i$. In step 310, the value of $X_j$ (the appropriate value of X for the precursor ion $X_j$) is calculated from Eq. 2. Subsequent steps 312, 314 and 316 respectively yield calculations of $P(x_j|a_i,X_j)$ (Eq. 3), $P(x_j|a_i)$ (Eqs. 4-6) and $P(a_i|x_j)$ (Eqs. 7-8), where the vectors $a_i$ and $x_j$ are the coefficient vectors, as previously defined, for the particular precursor ion, $a_i$, and particular product ion, $X_j$, respectively.

The calculated probabilities $P(a_i|x_j)$ can be used to deterministically (i.e., maximum likelihood) or randomly (i.e., Monte Carlo sampling) assign products to precursors for downstream analysis. FIG. 3 provides one example of such an assignment. In this example, after steps 308-316, have been completed then, if $P(a_i|x_j)$ is found, in step 318, to be above a certain possibly pre-defined threshold value, T, the product ion under consideration is assigned as having been produced from precursor ion $a_i$. The set of such assignments yield a synthetic MS/MS spectrum for the precursor ion $a_i$ in step 320. Subsequently, the method 600 loops back to step 304 in which another precursor ion is presented for consideration and the steps 306-320 are executed once again using this new precursor ion.

The set of products assigned to a given precursor can be thought of as synthetic MS/MS spectrum. The synthetic spectrum can be presented to an MS/MS identification program like Mascot or SEQUEST as if it were an observed spectrum. Analysis of the best hits can be used to update the probability estimates and iteratively redistribute the products among the precursors.

EXAMPLE 2

Pairwise Correlation Using at Least Partially Known Elemental Compositions

A feature of the following algorithm is the robust detection of pairwise complementary product ions using at least partially-known elemental composition (EC) analysis. In many cases, a precursor ion fragments into two stable product ions that are both detectable in an MS/MS spectrum. In spectra with high mass accuracy and resolving power, the ECs of the product and precursor ions can be inferred. When the sum of two product ion ECs is an exact match to a given precursor ion EC, it is possible to confidently identify these product ions as complementary and assign them to the corresponding precursor.

First, a sample comprising a mixture of parent ions is analyzed by tandem mass spectrometry using a mass spectrometer system such as is illustrated in FIGS. 1-2. The system is used so as to detect both precursor and product ions, possibly by performing separate precursor ion scans (to generate MS spectra) and product ion scans (to generate tandem or MS/MS spectra) as described above. In such a case, separate precursor ion and product ion mass spectra are obtained, the precursor spectrum containing peaks relating to a plurality of parent ions and the product spectrum containing "multiplexed" peaks relating to fragmentation products of all of or many of the precursors. Alternatively, the mass spectra may be obtained by performing partial fragmentation such that both precursor and product ion peaks are present in a single mass spectrum. In this case, precursor ions are identified by their much greater masses relative to the fragments.

Subsequently, the mass spectra are analyzed by the algorithm described below, comprising three phases: a first preprocessing phase (FIG. 4A) in which the mass, charge and variance of the mass is estimated for each respective precursor ion peak and product ion peak in the mass spectra; an accurate mass screen (FIG. 4B) for candidate pairs of complementary ions and a final phase (FIG. 4C) comprising a more rigorous test of these candidates using elemental composition analysis. The screening step is present to improve the time performance of the algorithm.

Figure 4A:
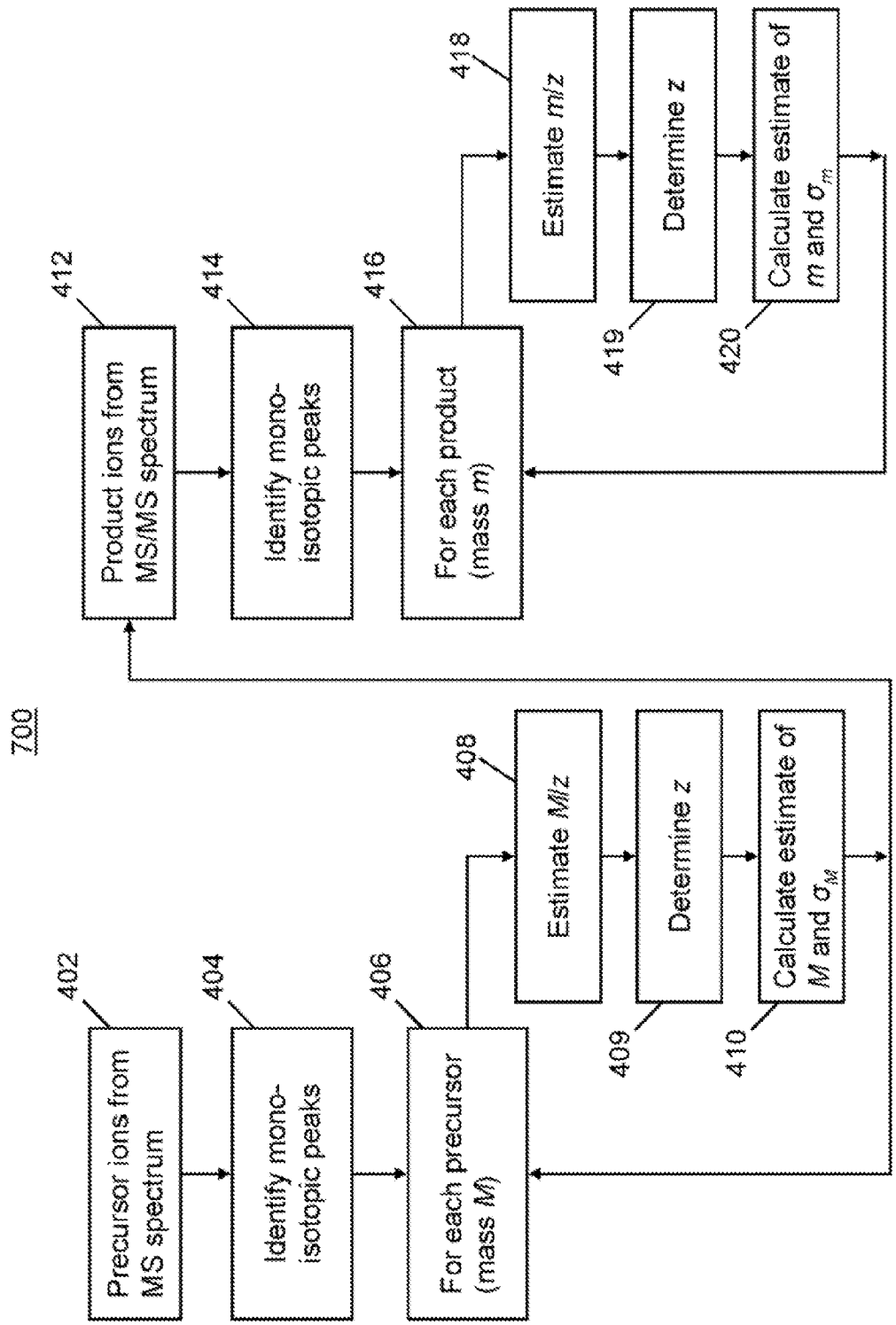
FIG. 4A is a flow chart illustrating steps comprising pre-processing of MS and MS/MS spectra in accordance with a second method for matching mass spectrometry precursor and product ions in accordance with the present invention.
Figure 4B:
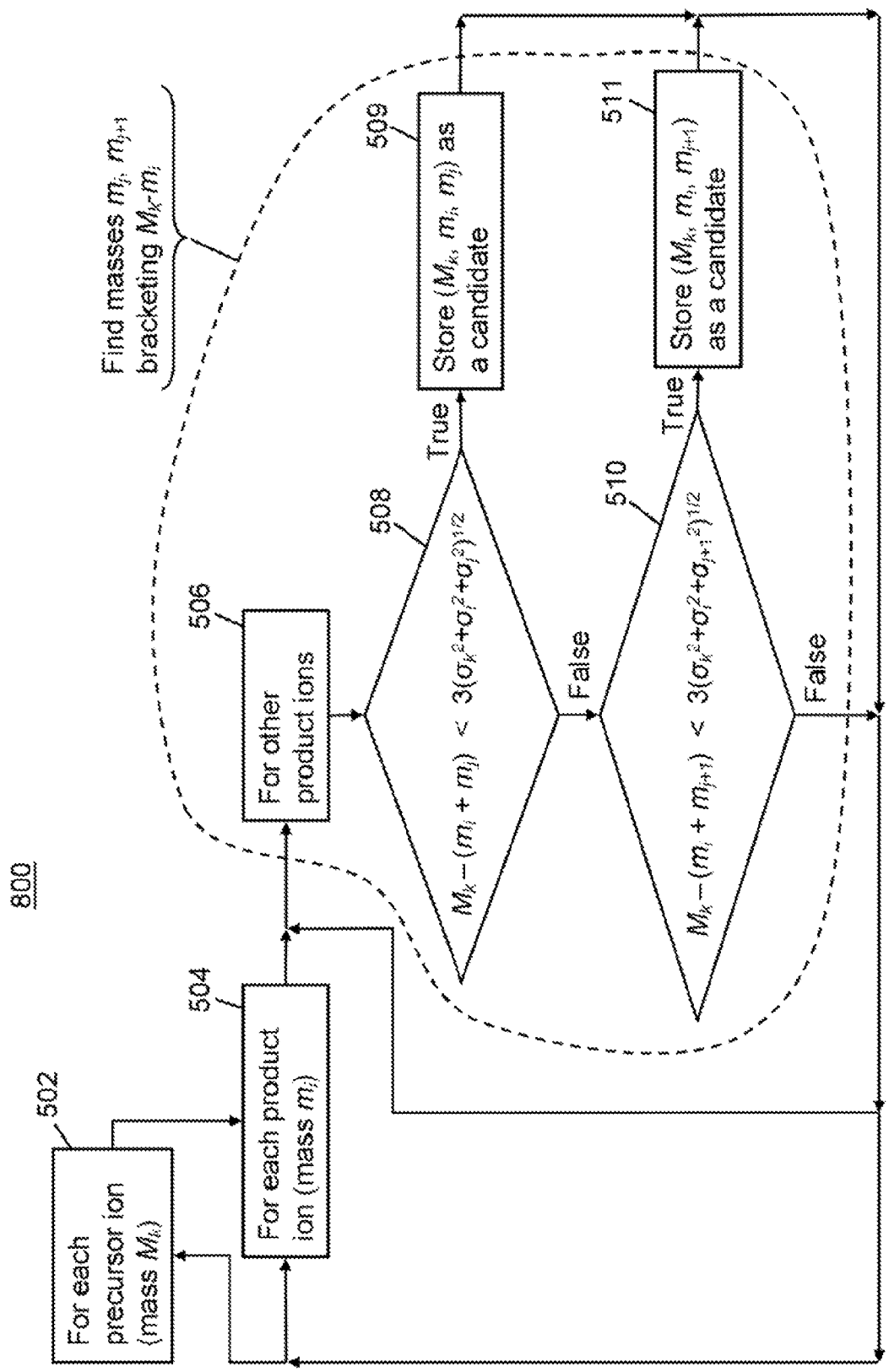
FIG. 4B is a flow chart illustrating steps comprising screening MS and MS/MS spectra for complementary product ions in accordance with the second method for matching mass spectrometry precursor and product ions in accordance with the present invention.

The preprocessing phase, specifically method 700 illustrated in FIG. 4A, comprises two separate stages—a first stage comprising steps 402 through 410 relating to precursor (parent) ions and a second stage comprising steps 412 through 420 relating to product ions. As may be observed from FIG. 4A, the steps are similar between the two stages. The two stages could be performed sequentially or simultaneously.

The steps 402 and 412, respectively relating to identification and extraction of precursor and product ion peaks from a single mass spectrum or from separate precursor and product mass spectra, are standard operations and have already been discussed. The next steps (step 404 and step 414) comprise identifying the monoisotopic peaks. In this regard, it is also assumed that the spectral peak corresponding to the monoisotopic species can be unambiguously determined. Then, for each monoisotopic ion (of mass $M_k$ for each of K precursor ions in step 406 or of mass $m_i$ for each of I product ions in step 416), determinations are made, in sequence, of $M_k/z_k$ (or $m_i/z_i$), of $z_k$ (or $z_i$) and finally, of $M_k$ and $\sigma_k$ (or $m_i$ and $\sigma_i$). These determinations are made in steps 408 through 410 for precursor ions and in steps 418 through 420 for product ions. The values of $M_k/z_k$ and $m_i/z_i$ (steps 408 and 418) may be derived directly from the mass spectra, using well-known calibration methods. The next analytic steps in the algorithm (steps 409 and 419) are the determination of the charge-state of each monoisotopic ion. For purposes of this determination, it is assumed that sufficient resolving power exists to resolve isotopic species that differ by one neutron. The difference in mass-to-charge ratio of such species is equal to the inverse of the charge. Therefore, the charge is determined by the inverse of the m/z spacing between adjacent peaks that are identified as isotopically related. Given the charge of the ion, the monoisotopic ion's measured mass-to-charge ratio can then be easily converted into an estimate of the mass of the neutral species (steps 410 and 420). In addition to estimates of neutral monoisotopic masses, it is also assumed that the uncertainties of the mass estimates are known or can be estimated.

Given the list of mass estimates and their uncertainties obtained as described above, it is possible to generate a list of candidate triplets (precursor, $product_1$, $product_2$) that could be related by the fragmentation reaction

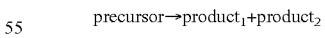

precursor→$product_1$+$product_2$

The magnitude of the estimated difference between the precursor mass and the sum of the two product masses should be similar to the uncertainties in the mass measurements. In particular, if $(M_k,\sigma_k^2)$, $(m_i,\sigma_i^2)$, and $(m_j,\sigma_j^2)$ denote the estimated mass and its variance for the precursor and two products respectively, then the difference $M_k-(m_i+m_j)$ would have variance $\sigma_k^2+\sigma_i^2+\sigma_j^2$. If the mass errors are normally distributed with zero mean, than it is statistically expected that more than 99% of related masses have differences less than three sigmas from the mean, i.e. $3(\sigma_k^2+\sigma_i^2+\sigma_j^2)^{1/2}$. Therefore, a threshold on the mass difference is used as a criterion for selecting candidates.

With the above background, it is possible to efficiently detect candidates from the list of precursor and product masses with a search algorithm (illustrated in FIG. 4B as method 800) that has computational complexity KN log N, where K and N are the number of precursor and product ions respectively, as described below. The steps 502 through 511 of method 800, which comprise an outer loop are performed for each precursor ion (e.g., with mass $M_k$). The steps 504 through 511, which comprise an inner nested loop, are performed for each product ion (e.g., with mass $m_i$). Thus, for each precursor and product ion, a search is conducted for other product ions (steps 506 through 511, comprising an innermost nested loop) whose mass is (approximately) equal to the mass difference $M_k - m_i$ within statistical limits. The search may be performed as a binary search on a list of product ions sorted by mass. The search (requiring at most log N steps) returns the two product ions whose masses bracket the required mass difference of the complementary fragment. If either of these masses differs from the target by less than the threshold (either step 508 or step 510), the triplet is retained as a candidate (steps 509 and 511).

It is reasonably expected that the number of product ions should be larger than the number of precursor ions (i.e., $N \gg K$), so the method described above would be faster than forming the pairwise sums of all product ions and then searching against the sorted precursor ion lists. This alternative suboptimal method would have complexity $N^2 \log K$ ($\gg KN \log N$).

In the next phase (FIG. 4C), the candidate triplets generated by the method 800 (FIG. 4B) are more rigorously screened by elemental composition determination. For example, suppose the elemental compositions of the precursor and two product ions are denoted by E, $e_1$, and $e_2$ respectively. The quantities E, $e_1$, and $e_2$ are vectors whose components are integer values specifying the number of atoms of various elemental types present in the respective neutral species. If the product ions are complementary fragments resulting from the precursor ion, their elemental compositions must sum (exactly) to the precursor elemental composition, i.e., $E = e_1 + e_2$. Equality of the vector sum requires equality of each component sum.

The isotope envelope is then used to assign probability to candidate elemental compositions for the precursors and products. The probability that the three indicated ions form a set related by a fragmentation reaction is given by Eq. 9

$$P = \sum_{E = e_2 + e_2} p(E) p(e_1) p(e_2) \quad \text{(Eq. 9)}$$

Each term in the probability sum is the product of three probability factors, each indicating the probability that a given elemental composition is correct. The terms in the sum reflect different possible combinations of elemental compositions that sum together as required by the fragmentation reaction.

Elemental composition determination is not a routine application in mass spectrometry. However, it should be noted that the potential number of elemental compositions increases rapidly with mass. So, in most cases, elemental composition determination is much more definitive for product ions than for precursor ions. The elemental compositions of some product ions cannot be determined with high confidence. Even though it may not be possible to exactly identify the elemental composition of a precursor ion, the observed isotope envelope often provides sufficient information to count heteroatoms, e.g., sulfur, or to count carbon atoms within 10-20% accuracy. In some cases, there is a priori information about possible elemental composition or molecular structure, e.g., proteomic or metabolic biotransformation databases. In combination, these constraints on product and precursor ions provide confident verification of a complementary relationship between them.

Figure 4C:
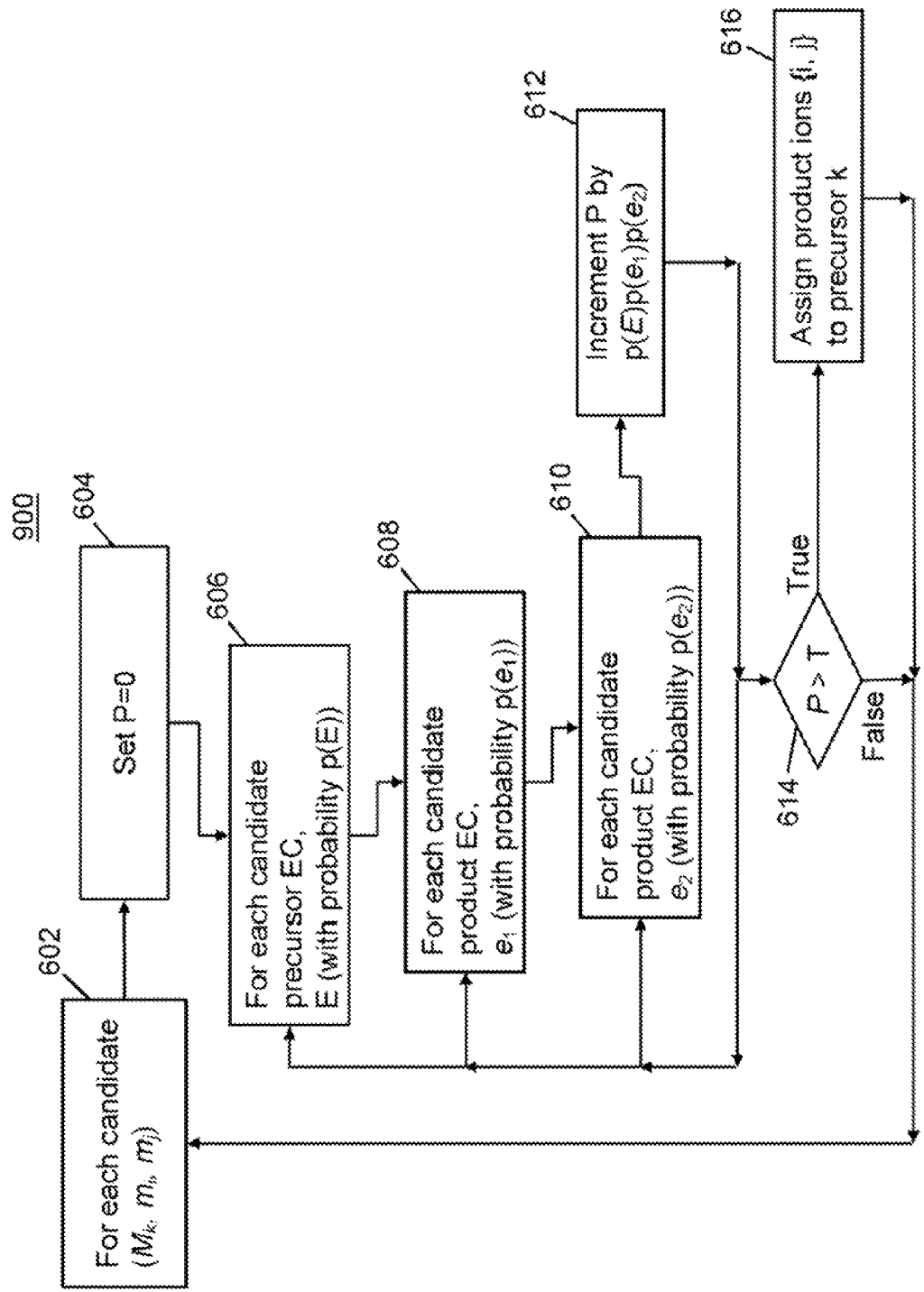
FIG. 4C is a flow chart illustrating steps comprising assessment of complementary product ion pair candidates by elemental composition analysis in accordance with the second method for matching mass spectrometry precursor and product ions in accordance with the present invention.

The method 900 illustrated in FIG. 4C formalizes these procedure outlined above. For each of the candidate triplets generated by the method 800 (FIG. 4B), there may exist several candidate elemental compositions (EC's), including candidate EC's for the candidate precursor and for each of the candidate products. The steps 602 through 616 form an outermost loop in which each candidate triplet ($M_k$, $m_i$, $m_j$) is evaluated in turn. Each of steps 606, 608 and 610 initiates a progressively nested inner loop in which candidate compositions are considered for the candidate precursor ion and for each of the candidate product ions, respectively. The result of this evaluation is, for each candidate triplet, the product P as given by equation Eq. 9. Step 612 calculates each term in the sum of Eq. 9 and adds it to the total sum calculated to that point. In step 614, if the probability P exceeds a certain pre-defined threshold T, then, in step 616, the product ions of the candidate triplet are identified as arising from the precursor ion.

Correct demultiplexing of a subset of the product ions, assigning them to their precursor ions, generates a collection of virtual MS/MS spectra, analogous to spectra that would be formed by the isolated product ions of each fragmented precursor. These virtual spectra are expected to contain fewer product ions than an actual MS/MS spectrum formed from an isolated precursor. Some product ions result from a "neutral loss" mechanism in which the complementary fragment is non-ionizable, and thus not detected by a mass spectrometer. In addition, other complementary fragments may be unstable, and thus not present at detectable levels. In other cases, the complementary fragment may be too small to be detected, i.e., below the lower limit of the spectrum's mass range. In each case where the complementary fragment is not detected, its partner fragment that appears in the actual isolated MS/MS spectrum is lost in the virtual demultiplexed MS/MS spectrum.

By assigning pairs of complementary product ions to precursors, the multiplex MS/MS spectrum is demultiplexed to form "virtual" MS/MS spectra, each corresponding to an MS/MS spectrum from an isolated precursor. Each virtual MS/MS spectrum can be submitted to standard algorithms, such as MASCOT and SEQUEST, which identify precursors from MS/MS spectra. Despite the multiple mechanisms of product ion loss described above, there is often enough product ions in demultiplexed spectra to provide confident precursor identification (cite Zubarev.)

EXAMPLE 3

Experimental Implementation

One proposed experiment of this type performs multiple injections of distinct precursor ions, each individually isolated, to create a mixture of precursor ions that are simultaneously fragmented and analyzed. Another experiment performs coarse isolation (e.g., selecting ions residing in a band of tens to hundreds of m/z units) to create a mixture of precursor ions whose products are analyzed together as before. A third type of experiment involves the Exactive™ mass spectrometer, a standalone Orbitrap mass analyzer, which does not provide capability for isolation before fragmentation of ions in its HCD collision cell and subsequent analysis.

The workflow described on the Exactive mass spectrometer provides the ability to perform detailed identification and accurate quantification by alternating two types of scans at high frequency (e.g. 5 Hz). The first scan type is a precursor scan in which ions flow directly from the ion source into the analytic cell. The second scan type is an "all ions" fragmentation scan in which all ions (without mass filtering) flow into the HCD cell (i.e., reaction cell 150) where they are broken into products by collisions with neutral gas molecules. The resulting products are then transported into the analytic cell. The analysis of precursors at a high scan rate (combining every other scan, i.e., scans of only the first type) allows accurate integration of chromatographic peak shapes at decreased run times. The analysis of products for all precursors provides extensive identification coverage.

The discussion herein is intended to serve as a basic description. Although the invention has been described in accordance with the various embodiments put forth herein, one of ordinary skill in the art will readily recognize that there could be variations to the embodiments and those variations would be within the scope of the present invention. The specific discussions herein may not explicitly describe all embodiments possible; many alternatives are implicit. Accordingly, many modifications may be made by one of ordinary skill in the art without departing from scope and essence of the invention. Neither the description nor the terminology is intended to limit the scope of the invention. Any patents, patent application publications or other publications are hereby explicitly incorporated herein by reference in their entirety as if set forth fully herein.

What is claimed is:

1. A method of tandem mass spectrometry (MS/MS) for use in a mass spectrometer characterized by the steps:
   (a) repeating, a finite number of times, the steps of:
      (a1) selecting a distinct mass to charge (m/z) ratio;
      (a2) isolating a set of precursor ions of a precursor ion type, said precursor ions of said precursor ion type comprising said m/z ratio;
      (a3) estimating an elemental composition for the precursor ions comprising said (m/z) ratio, the estimation based on said m/z ratio and an estimated charge state; and
      (a4) transferring said isolated precursor ions into an ion storage device, so as to create a mixture of precursor ion types therein, the mixture including any precursor ions previously transferred into the ion storage device;
   (b) generating fragment ions comprising plurality of fragment ion types by fragmenting the plurality of precursor ion types of the mixture;
   (c) generating a mass spectrum of the fragment ion types so as to determine a respective m/z ratio or m/z ratio range for each respective fragment ion type;
   (d) estimating an elemental composition for each of the fragment ion types based on the determined m/z ratio or m/z ratio range and an estimated charge state for each respective fragment ion type; and
   (e) calculating a set of probability values for each precursor ion type, each probability value representing a probability that a respective fragment ion type or a respective pair of fragment ion types was derived from the precursor ion type.

2. A method of tandem mass spectrometry as recited in claim 1, further characterized by the step:
   (f) generating a synthetic MS/MS spectrum for each respective precursor ion type based on the calculated probability values.

3. A method of tandem mass spectrometry as recited in claim 2, further characterized by the step:
   (g) providing at least one of the synthetic MS/MS spectra as input to a peptide identification software product so as to identify a peptide.

4. A method of tandem mass spectrometry as recited in claim 1, wherein the mass spectrometer provides a mass accuracy of 1 part-per-million or better.

5. A method of tandem mass spectrometry as recited in claim 1, wherein the mass spectrometer comprises an ion cyclotron resonance mass spectrometers or an electrostatic trap mass spectrometer.

6. A method of tandem mass spectrometry (MS/MS) for use in a mass spectrometer characterized by the steps:
   (a) repeating, a finite number of times, the steps of:
      (a1) selecting a distinct mass to charge (m/z) ratio;
      (a2) isolating a set of precursor ions of a precursor ion type, said precursor ions of said precursor ion type comprising said m/z ratio;
      (a3) estimating an elemental composition for the precursor ions comprising said (m/z) ratio, the estimation based on said m/z ratio and an estimated charge state; and
      (a4) transferring said isolated precursor ions into an ion storage device, so as to create a mixture of precursor ion types therein, the mixture including any precursor ions previously transferred into the ion storage device;
   (b) generating fragment ions comprising plurality of fragment ion types by fragmenting the plurality of precursor ion types of the mixture;
   (c) generating a mass spectrum of the fragment ion types so as to determine a respective m/z ratio or m/z ratio range for each respective fragment ion type;
   (d) estimating an elemental composition for each of the fragment ion types based on the determined m/z ratio or m/z ratio range and an estimated charge state for each respective fragment ion type; and
   (e) calculating a set of probability values for each fragment ion type, each probability value representing a probability that the fragment ion type was derived from a respective one of the precursor ion types.

7. A method of tandem mass spectrometry as recited in claim 6, further characterized by the step:
   (f) generating a synthetic MS/MS spectrum for each respective fragment ion type based on the calculated probability values.

8. A method of tandem mass spectrometry as recited in claim 7, further characterized by the step:
   (g) providing at least one of the synthetic MS/MS spectra as input to a peptide identification software product so as to identify a peptide.

9. A method of tandem mass spectrometry as recited in claim 6, wherein the mass spectrometer provides a mass accuracy of 1 part-per-million or better.

10. A method of tandem mass spectrometry as recited in claim 6, wherein the mass spectrometer comprises an ion cyclotron resonance mass spectrometers or an electrostatic trap mass spectrometer.

* * * * *